(12) United States Patent
Murray et al.

(10) Patent No.: US 8,038,989 B2
(45) Date of Patent: Oct. 18, 2011

(54) HAIR CONDITIONING COMPOSITIONS

(75) Inventors: Andrew Malcolm Murray, Wirral (GB); Thuy-Anh Pham, Wirral (GB); Smita Puntambekar, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 349 days.

(21) Appl. No.: 12/152,544

(22) Filed: May 15, 2008

(65) Prior Publication Data

US 2008/0311067 A1 Dec. 18, 2008

(30) Foreign Application Priority Data

May 25, 2007 (EP) .................................... 07108906

(51) Int. Cl.
*A61K 8/18* (2006.01)
(52) U.S. Cl. .................................. 424/70.27
(58) Field of Classification Search .............. None
See application file for complete search history.

(56) References Cited

U.S. PATENT DOCUMENTS 6,923,954 B2* 8/2005 Doi et al. .................... 424/70.19
2002/0034485 A1* 3/2002 Noser et al. ................. 424/70.1

FOREIGN PATENT DOCUMENTS

| DE | 196 41 841 | 10/1997 |
|---|---|---|
| EP | 0 412 705 | 2/1991 |
| EP | 0 412 706 | 2/1991 |
| EP | 0 412 710 | 2/1991 |
| JP | 2002 226327 | 8/2002 |
| WO | 95/20939 | 8/1995 |
| WO | 99/44568 | 9/1999 |
| WO | 01/17502 | 3/2001 |

OTHER PUBLICATIONS

PCT International Search Report in PCT application PCT/EP2008/056251.

* cited by examiner

*Primary Examiner* — Tracy Vivlemore
*Assistant Examiner* — Jennifer Berrios
(74) *Attorney, Agent, or Firm* — Ronald A. Koatz

(57) ABSTRACT

The invention provides a hair conditioning composition comprising an aqueous carrier, a lamellar gel phase formed from cationic surfactant and fatty material and a rheology modifier for the lamellar gel phase which comprises a fatty acid and a water-soluble, nonionic polymer of alkylene oxide of the general formula:

$$H(OCH_2CHR)_nOH$$

in which R is H, methyl, or mixtures thereof, and n has an average value of at least 150.

Compositions of the invention provide a superior viscosity profile.

4 Claims, No Drawings

HAIR CONDITIONING COMPOSITIONS

FIELD OF THE INVENTION

The present invention relates to hair conditioning compositions which comprise a fatty acid and a water-soluble nonionic polymer.

BACKGROUND TO THE INVENTION AND PRIOR ART

Hair conditioning compositions are typically applied to the hair immediately after shampooing and rinsing the hair. The conditioning composition is worked through the hair, and may then be left to penetrate the hair for a period of time before rinsing it from the hair with water.

Traditionally such conditioning compositions have used a combination of cationic surfactants and fatty materials, typically long chain fatty alcohols. This combination forms a lamellar gel phase which imparts a desirable viscosity to the product and deposits on the hair during use of the product to provide a conditioning benefit.

Many consumers desire a "lighter" conditioning product which imparts less of a slippery and coated feel to their hair. This has led to the development of "low-fat" formulations with a reduced content of fatty material.

However, reducing the content of fatty material can also reduce the viscosity of the product to an unacceptable level. Consequently, it has been found to be necessary to incorporate a thickener.

Examples of thickeners which have been used for this purpose are nonionic cellulose ethers such as hydroxyethylcellulose.

Hydrophobically-modified cellulose ethers such as cetyl hydroxyethylcellulose have also been used. Materials of this type are described in EP 412 705, EP 412 706 and EP 412 710 as providing a rheology very much like the gel-network structure of typical hair conditioners without the slimy feel associated with most polymeric thickeners, and without using a typical quaternary ammonium compound/fatty alcohol gel-network thickening system.

A problem associated with hair conditioning compositions such as those described above is that it is difficult to obtain the right viscosity profile under different conditions of product usage. For example, a thick, creamy product viscosity is desirable to enable controlled pouring and product dosage onto the hair. However, in order to facilitate spreading of the product through the hair and rinsing, it is desirable that the product viscosity breaks down rapidly on dilution. If the product is difficult to rinse from the hair, then this may contribute to sensory negatives perceived by the consumer such as a dirty, "coated" hair feel after use.

The inventors have found that this problem can be solved by incorporating a fatty acid and a water-soluble, nonionic polymer of alkylene oxide into the hair conditioning composition.

JP2002226327 describes a hair cosmetic which is readily pourable, which has a rich product feel on the hand, and which provides a smooth hair feel after rinsing and drying. The cosmetic incorporates a higher fatty acid having a hydroxyl group in a side chain, such as 12-hydroxystearic acid.

DE19641841 describes an aqueous composition comprising 10 to 26 C fatty acid, in combination with directly acting hair dye and certain alcohol or glycol ether solvents. The composition is said to provide good conditioning and hair dyeing effects.

WO99/44568 relates to the use of water-soluble nonionic polyethyleneoxide homopolymers to increase hair body and fullness when formulated in a high pH medium and applied to fine hair. They are said to deposit under the hair cuticle and provide it with more surface roughness and texture.

WO95/20939 describes thickened cream rinse emulsions with a combination of low melting point fatty alcohol with polyethyleneoxide homopolymers. The emulsions are said to provide excellent wet hair feel, spreadability, and rinseability, as well as providing glossiness, hair alignment, and volume reduction, and especially dry combing benefits.

SUMMARY OF THE INVENTION

The invention provides a hair conditioning composition comprising an aqueous carrier, a lamellar gel phase formed from cationic surfactant and fatty material and a rheology modifier for the lamellar gel phase which comprises a fatty acid and a water-soluble, nonionic polymer of alkylene oxide of the general formula:

$$H(OCH_2CHR)_nOH$$

in which R is H, methyl, or mixtures thereof, and n has an average value of at least 150.

DETAILED DESCRIPTION OF THE INVENTION

Cationic Surfactant

Compositions according to the invention comprise one or more cationic surfactants which are cosmetically acceptable and suitable for topical application to the hair.

The cationic surfactant, together with the fatty material and the aqueous carrier, forms a lamellar gel phase which is suitable for providing various hair conditioning attributes.

Suitable cationic surfactants for use in compositions of the invention contain amino or quaternary ammonium hydrophilic moieties which are positively charged when dissolved in the composition.

Suitable quaternary ammonium cationic surfactants correspond to the following general formula:

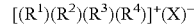

$$[(R^1)(R^2)(R^3)(R^4)]^+(X)^-$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

In a suitable class of cationic surfactant of general formula (I), $R^1$ and $R^2$ are each independently selected from $C_{16}$ to $C_{22}$ hydrocarbyl chains comprising at least one ester linkage in both $R^1$ and $R^2$, and $R^3$ and $R^4$ are each independently selected from $CH_3$ and $CH_2CH_2OH$.

In another suitable class of cationic surfactant of general formula (I), $R^1$ and $R^2$ are each independently selected from $C_{16}$ to $C_{22}$ saturated or unsaturated, preferably saturated, chains, and $R^3$ and $R^4$ are each independently selected from $CH_3$ and $CH_2CH_2OH$, preferably $CH_3$.

In a preferred class of cationic surfactant of general formula (I), $R^1$ is a $C_{16}$ to $C_{22}$ alkyl chain and $R^2$, $R^3$ and $R^4$ are each independently selected from $CH_3$ and $CH_2CH_2OH$, preferably $CH_3$.

Specific examples of suitable quaternary ammonium cationic surfactants of general formula (I) are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

Particularly preferred quaternary ammonium cationic surfactants for use in the invention are cetyltrimethylammonium chloride, available commercially, for example as GENAMIN CTAC, ex Hoechst Celanese and Arquad 16/29 supplied by Akzo Nobel, and behenyltrimethylammonium chloride (BTAC) such as Genamin KDM-P supplied by Clariant.

Mixtures of any of the foregoing materials may also be suitable.

Salts of primary, secondary, and tertiary fatty amines are also suitable cationic surfactants for use in the invention. The alkyl groups of such amines preferably have from about 12 to about 22 carbon atoms, and can be substituted or unsubstituted. These amines are typically used in combination with an acid to provide the cationic species.

A preferred class of amine corresponds to the following general formula:

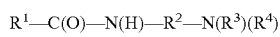

$R^1$—C(O)—N(H)—$R^2$—N($R^3$)($R^4$)

in which $R^1$ is a fatty acid chain containing from 12 to 22 carbon atoms, $R^2$ is an alkylene group containing from one to four carbon atoms, and $R^3$ and $R^4$ are, independently, an alkyl group having from one to four carbon atoms.

Specific examples of suitable materials of general formula (II) are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

Particularly preferred is stearamidopropyldimethylamine.

Mixtures of any of the foregoing materials may also be suitable.

The acid used to provide the cationic species can be any organic acid or mineral acid of sufficient acid strength to neutralise a free amine nitrogen. Such acids include hydrochloric acid, sulphuric acid, nitric acid, phosphoric acid, lactic acid, citric acid, tartaric acid, acetic acid, gluconic acid, glycolic acid and propionic acid, or combinations thereof. In general, a sufficient amount of acid is added to neutralise the amidoamine compound and to adjust the final pH of the composition to within a range of from about 2.5 to about 6, preferably in a pH range of from about 3 to about 5. The molar ratio of protonatable amine groups to $H^+$ from the acid is preferably from about 1:0.3 to 1:1.2, and more preferably from about 1:0.5 to about 1:1.1.

Mixtures of any of the above-described cationic surfactants may also be suitable.

In the composition of the invention, the level of cationic surfactant preferably ranges from 0.1 to 10%, more preferably 0.2 to 5%, most preferably 0.25 to 4% by total weight of cationic surfactant based on the total weight of the composition.

Fatty Material

Compositions of the invention comprise a fatty material.

The fatty material, together with the cationic surfactant and the aqueous carrier, forms a lamellar gel phase which is suitable for providing various hair conditioning attributes.

By "fatty material" is meant a compound having the general formula R—X, wherein R is an aliphatic carbon chain and X is a functional group (e.g. alcohol or derivative), and which is different from the fatty acid of the rheology modifier.

R is preferably a saturated aliphatic carbon chain comprising from 8 to 30 carbon atoms, more preferably from 16 to 22 carbon atoms.

R can contain, in addition to carbon and hydrogen atoms, ether linkages, and other groups such as amino groups. Preferably R is a hydrocarbon chain.

X is preferably a hydroxyl group.

Most preferably, the fatty material is a fatty alcohol of general formula $CH_3(CH_2)_nOH$, where n is an integer from 7 to 29, preferably from 15 to 21.

Specific examples of suitable fatty alcohols are cetyl alcohol, stearyl alcohol, behenyl alcohol, and mixtures thereof.

The level of fatty material in conditioners of the invention suitably ranges from 0.01 to 15%, preferably from 0.1 to 10%, and more preferably from 0.5 to 4% by total weight fatty material based on the total weight of the composition.

Fatty Acid

Compositions of the invention comprise a rheology modifier for the lamellar gel phase which comprises a fatty acid.

Preferred fatty acids have the general formula R—COOH, in which R is a saturated aliphatic $C_{12}$ to $C_{22}$ hydrocarbon chain (hereinafter referred to as a "saturated aliphatic C12 to C22 fatty acid").

More preferably, the fatty acid has the general formula $CH_3(CH_2)_nCOOH$, where n is an integer from 14 to 20.

Specific examples of suitable fatty acids are palmitic acid, stearic acid and behenic acid, and mixtures thereof.

The level of fatty acid in conditioners of the invention suitably ranges from 0.01 to 15%, preferably from 0.05 to 10%, and more preferably from 0.3 to 1.2% by total weight saturated aliphatic C12 to C22 fatty acid based on the total weight of the composition.

The combined level of fatty material and fatty acid in conditioners of the invention suitably ranges from 0.01 to 15%, preferably from 0.5 to 10%, and more preferably from 1.5 to 4.5% by total weight (fatty material and fatty acid) based on the total weight of the composition.

The weight ratio of (fatty material):(fatty acid) in conditioners of the invention is suitably from 1:5 to 10:1, preferably from 1:2 to 8:1, more preferably from 1:1 to 6.5:1.

The weight ratio of (cationic surfactant):(fatty material and fatty acid) is suitably from 10:1 to 1:10, preferably from 4:1 to 1:8, more preferably from 1:1 to 1:7.

Water-Soluble, Nonionic Polymer of Alkylene Oxide

Compositions of the invention comprise a rheology modifier for the lamellar gel phase which comprises a water-soluble, nonionic polymer of alkylene oxide of the general formula:

$$H(OCH_2CHR)_nOH$$

in which R is H, methyl, or mixtures thereof, and n has an average value of at least 150.

As used herein, "water-soluble" refers to any material that is sufficiently soluble in water to form a clear or translucent solution to the naked eye at a concentration of 1.0% or more by weight of the material in water at 25° C.

When R is H, these materials are polymers of ethylene oxide, which are also known as polyethyleneoxides, polyoxyethylenes, and polyethylene glycols.

When R is methyl, these materials are polymers of propylene oxide, which are also known as polypropyleneoxides, polyoxypropylenes, and polypropylene glycols. When R is methyl, various positional isomers of the resulting polymers can exist.

In the above structure, R is most preferably H.

In the above structure, n may typically have an average value of from about 150 to about 235,000, preferably from about 2,000 to about 225,000, more preferably from about 40,000 to about 185,000.

Examples of commercially available polymers of alkylene oxide suitable for use in the invention include those polyethyleneoxides which are sold under the tradenames POLYOX® and UCARFLOC®, and which are available from the Dow Chemical Company or its associated companies.

Specific examples of such materials which are suitable for use in the invention include POLYOX® WSR-N10 (where n has an average value of about 2000, also known as PEG-2M); POLYOX® WSR-N80 (where n has an average value of about 5000, also known as PEG-5M); POLYOX® WSR-N750 (where n has an average value of about 7000, also known as PEG-7M); POLYOX® WSR-N3000 (where n has an average value of about 14,000, also known as PEG-14M); POLYOX® WSR-N12K (where n has an average value of about 23,000, also known as PEG-23M); POLYOX® WSR-N60K (where n has an average value of about 45,000, also known as PEG-45M); POLYOX® WSR-301 (where n has an average value of about 90,000, also known as PEG-90M); POLYOX® WSR-303; POLYOX® WSR-308 (where n has an average value of about 180,000, also known as PEG-180M); UCARFLOC® Polymer 304; UCARFLOC® Polymer 309 (where n has an average value of about 180,000, also known as PEG-180M) and UCARFLOC® Polymer 310 (where n has an average value of about 225,000, also known as PEG-225M).

Mixtures of any of the above polymers of alkylene oxide may also be suitable.

The total amount of water-soluble, nonionic polymer of alkylene oxide in compositions of the invention generally ranges from 0.001 to 1%, preferably from 0.002 to 2%, more preferably from 0.005 to 0.1%, and most preferably from 0.01 to 0.05%, by total weight polymer of alkylene oxide based on the total weight of the composition.

Aqueous Carrier

The conditioning composition of the present invention comprises an aqueous carrier.

Suitable aqueous carriers are water and water solutions of lower alkyl alcohols and polyhydric alcohols.

Examples of suitable lower alkyl alcohols are monohydric alcohols having 1 to 6 carbons, preferably ethanol and isopropanol.

Examples of suitable polyhydric alcohols are propylene glycol, hexylene glycol, glycerin, and propanediol.

Preferably, the aqueous carrier is substantially water.

Generally, compositions according to the invention comprise at least 60%, preferably at least 65%, more preferably at least 70% water by weight based on the total weight of the composition.

Additional Conditioning Agents

Compositions of the invention may comprise additional conditioning agents to optimise wet and dry conditioning benefits.

Particularly preferred further conditioning agents are silicone emulsions.

Suitable silicone emulsions include those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone.

The emulsion droplets may typically have a Sauter mean droplet diameter ($D_{3,2}$) in the composition of the invention ranging from 0.01 to 20 micrometer, more preferably from 0.2 to 10 micrometer.

A suitable method for measuring the Sauter mean droplet diameter ($D_{3,2}$) is by laser light scattering using an instrument such as a Malvern Mastersizer.

Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

$$HO[CH_2CH_2O]_x[CH(CH_3)CH_2O]_y[CH_2CH_2O]_xH$$

wherein the mean value of x is 4 or more and the mean value of y is 25 or more.

Another preferred form of the surface active block copolymer is according to the following formula:

$$(HO[CH_2CH_2O]_a[CH(CH_3)CH_2O]_b)_2-N-CH_2-CH_2-N([OCH_2CH(CH_3)]_b[OCH_2CH_2]_aOH)_2$$

wherein the mean value of a is 2 or more and the mean value of b is 6 or more.

Mixtures of any of the above described silicone emulsions may also be used.

Silicone will generally be present in a composition of the invention at levels of from 0.05 to 10%, preferably 0.05 to 5%, more preferably from 0.5 to 2% by total weight of silicone based on the total weight of the composition.

Other Optional Ingredients

Compositions according to the invention may also incorporate other cosmetically suitable ingredients, preferably at a level of 2% by weight or less. Suitable ingredients include: preservatives, colouring agents, chelating agents, antioxidants, fragrances, antimicrobials, antidandruff agents, cationic conditioning polymers, styling ingredients, sunscreens, proteins and hydrolysed proteins.

Use

The compositions of the invention may be used by applying them to wet hair, preferably hair which has been shampooed and then rinsed with water.

Generally, the composition is applied to the hair (preferably hair which has been shampooed and then rinsed with water), and then worked through the hair. Preferably the composition is then left to penetrate the hair for a period of about one to three minutes before rinsing it from the hair with water.

The invention will now be further described by reference to the following Examples. In the Examples, all percentages are by weight based on total weight, unless otherwise specified. Examples according to the invention are denoted by a number, whereas comparative examples are denoted by a letter.

EXAMPLES

A series of hair conditioning compositions were prepared having ingredients as shown in the following Table 1:

TABLE 1

| Ingredient | A | B | 1 | C | D | 2 | 3 | 4 |
|---|---|---|---|---|---|---|---|---|
| Cetyl trimethyl ammonium chloride (29% active) | 2.4 | 2.4 | 2.4 | — | — | — | 3.448 | 3.448 |
| Behenyl trimethyl ammonium chloride (80% active) | — | — | — | 0.875 | 0.875 | 0.875 | — | — |
| Cetearyl alcohol | 3 | 1.575 | 1.575 | — | — | — | 2.25 | 2.25 |
| Cetostearyl alcohol | — | — | — | 2.1 | 1.68 | 1.68 | — | — |
| Stearic Acid (97% active) | — | 0.541 | 0.541 | — | 0.433 | 0.433 | 0.773 | 0.773 |
| PEG-180M[(1)] | — | — | 0.02 | — | — | 0.02 | 0.02 | — |
| PEG-45M[(1)] | — | — | — | — | — | — | — | 0.02 |
| Silicone (60% active) | 2.5 | 2.5 | 2.5 | 2.5 | 2.5 | 2.5 | 2.5 | 2.5 |
| POLYSURF ® 67[(2)] | 0.03 | — | — | 0.06 | — | — | — | — |
| Phenoxyethanol | 0.4 | 0.4 | 0.4 | — | — | — | 0.4 | 0.4 |
| Methyl Paraben | — | — | — | 0.2 | 0.2 | 0.2 | — | — |
| Perfume | 0.5 | 0.5 | 0.5 | 0.5 | 0.5 | 0.5 | 0.5 | 0.5 |
| pH adjuster | to give pH of about 3 to 6 | | | | | | | |
| Water | to 100 | | | | | | | |

[(1)]ex Dow Chemical Company
[(2)]Cetyl hydroxyethylcellulose, ex Aqualon

The compositions were evaluated for their viscosity behaviour on dilution. Neat viscosity and viscosity at 1 in 4 dilution (with water) was measured and compared for each composition. The results of the evaluation are shown below in Table 2.

TABLE 2

| Example | Log (Neat Viscosity) − Log (Viscosity at 1 in 4 Dilution) |
|---|---|
| A | 1.27 |
| B | 2.31 |
| 1 | 5.31 |
| C | 2.01 |
| D | 3.91 |

TABLE 2-continued

| Example | Log (Neat Viscosity) − Log (Viscosity at 1 in 4 Dilution) |
|---|---|
| 2 | 5.38 |
| 3 | 5.52 |
| 4 | 5.54 |

The results show that the Examples according to the invention (1 and 2) give a faster viscosity drop on dilution, when compared to Comparative Examples (A, B, C, D) with equivalent cationic surfactant bases. The compositions according to the invention (1 to 4) have a viscosity which breaks down rapidly on dilution. This effect facilitates fast rinsing of the product from the hair by the consumer. The effect is observed for compositions of the invention over a range of different cationic surfactant bases and molecular weights of the polyethylene glycol polymer.

The invention claimed is:

1. A hair conditioning composition comprising an aqueous carrier, a lamellar gel phase form from a cationic surfactant and fatty material and a rheology modifier for the lamellar gel phase which comprises a fatty acid and a water-soluble, non-ionic polymer of alkylene oxide of the general formula:

$$H(OCH2CHR)nOH,$$

in which R is H and n has an average value of 40,000 to 180,000, wherein said fatty acid is stearic acid.

2. A hair conditioning composition according to claim 1, in which the cationic surfactant is a quaternary ammonium cationic surfactant corresponding to the following general formula (I):

$$[N(R^1)(R^2)(R^3)(R^4)]^+(X)^- \qquad (I)$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g, chloride, bromide), acetate, citrate, lactate, glycolate, phosphate nitrate, sulphate, and alkylsulphate radicals.

3. A hair conditioning composition according to claim 1, in which the cationic surfactant is a salt of an amine corresponding to the following general formula (II):

$$R^1\text{—C(O)—N(H)—}R^2\text{—N}(R^3)(R^4) \tag{II}$$

in which $R^1$ is a fatty acid chain containing from 12 to 22 carbon atoms, $R^2$ is an alkylene group containing from one to four carbon atoms, and $R^3$ and $R^4$ are, independently, an alkyl group having from one to four carbon atoms.

4. A hair conditioning composition according to claim 1, in which the fatty material is a fatty alcohol of general formula $CH_3(CH_2)_nOH$, where n is an integer from 7 to 29.

* * * * *